(12) United States Patent
Chan et al.

(10) Patent No.: US 6,733,647 B2
(45) Date of Patent: May 11, 2004

(54) ELECTROPHORESIS GELS

(75) Inventors: Grace Yim Ngan Chan, Highton (AU); Nicola Sarah Frances Boyd, Baulkham Hills (AU); Sue Ann Gooley, Kingsford (AU); David Henry Solomon, Officer (AU)

(73) Assignee: Gradipore, Ltd., Frenchs Forest (AU)

(*) Notice: Subject to any disclaimer, the term of this patent is extended or adjusted under 35 U.S.C. 154(b) by 317 days.

(21) Appl. No.: 09/785,761

(22) Filed: Feb. 16, 2001

(65) Prior Publication Data

US 2001/0027921 A1 Oct. 11, 2001

(30) Foreign Application Priority Data

Feb. 18, 2000 (AU) .............................................. PQ5714

(51) Int. Cl.[7] ............................................ G01N 27/447
(52) U.S. Cl. ........................ 204/606; 204/616; 204/470
(58) Field of Search ................................ 204/455–461, 204/466, 468–470, 605–612, 616–618

(56) References Cited

U.S. PATENT DOCUMENTS

| 3,948,743 A | 4/1976 | Monthony et al. ........... 204/469 |
| 5,543,097 A | 8/1996 | Fang ........................ 264/102 |
| 5,578,180 A | 11/1996 | Engelhorn et al. .......... 204/468 |
| 5,660,702 A | * 8/1997 | Starr ........................ 204/469 |

FOREIGN PATENT DOCUMENTS

DE  4112168 A1  10/1992

OTHER PUBLICATIONS

English language translation of Balshuesemann (DE 4112168 A1).*
Pages 79–81 of Electrophoresis: Theory, Techniques, and Biochemical and Clinical Applications, 2nd ed., Anthony Andrews, Clarendon Press–Oxford, 1986.*
CAPLUS abstract of Rosengren et al. ("A simple method of choosing optimum pH–conditions for electrophoresis," Electrofocusing Isotachophoresis, Proc. Int. Symp. (1977), Meeting Date 1976, 165–71. Eds. Radola et al.*
Starzec et al. ("Several Intermediate Forms in the Processing of Rat Lutropin Subunits as shown by Sodium Dodecyl Sulphate Polyacrylamide Gel Electrophoresis," Journal of Chromatography, 440 (1988) 353–360).*
Wadstrom et al. (A rapid method for separation and detection of human amylase isoenzymes by isoelectric focusing in polyacrylamide gel, Scand. J. Dent. Res. 1976: 234–239.*
Biological Buffers, p. 7–9 of the third electronic edition of the CRC Handbook of Chemistry and Physics.*
DialogIP Document; English abstract for EP509388.

* cited by examiner

Primary Examiner—Alex Noguerola
(74) Attorney, Agent, or Firm—Baker & McKenzie

(57) ABSTRACT

A polyacrylamide gel utilizing a buffer system comprising Tris(hydroxymethyl)aminomethane at the concentration range 0.15 to 0.25 M titrated with hydrochloric acid to a pH between 6.5 and 7.5. The gel is substantially stable to polyacrylamide hydrolysis during storage for at extended periods and has an acceptable shelf-life of at least 6 months after storage at about 4° C.

9 Claims, 4 Drawing Sheets

ELECTROPHORESIS GELS

TECHNICAL FIELD

This invention relates to the field of gel electrophoresis, particularly to pre-cast polyacrylamide gels having an extended shelf-life.

BACKGROUND ART

Gel electrophoresis is an important analytical and preparative separation technique in which charged molecules are separated under the influence of an electric field with a gel being used as the support matrix. This technique is particularly suitable for the separation of biological macromolecules. The gels commonly used in this technique are composed of polyacrylamide or agarose. Polyacrylamide gels are used particularly for the separation of biomolecules such as proteins, peptides, DNA, RNA, lipids, charged carbohydrates and the like, either naturally occurring or synthetic, in which the acrylamide is used in slab form being pre-cast prior to use. Traditionally, polyacrylamide gels have been prepared individually prior to use by polymerising an acrylamide/cross-linker solution in a gel-casting cassette to form a slab. Following electrophoresis, the gels are removed from the cassette, and the biomolecules are stained and/or transferred from the gel to another medium so that the separated biomolecules may be visualised, identified, recovered or quantified. Conventional polyacrylamide gels have the disadvantage of being relatively unstable and have a limited shelf-life.

As gels are often prepared on an individual basis prior to use, there can be variations between gels that have been cast separately such that direct comparisons between separations using different gels are not reliable. Furthermore, the monomer components in polyacrylamide gels are relatively toxic and continued preparation of gels increases the potential of exposure of these toxic monomers to the operator. There has now been a move to the commercial preparation of pre-cast gels under controlled conditions providing consistent and stable characteristics between batches of gels. Unfortunately, most pre-cast commercial gels still have the problem of limited shelf-life and must be used within a relatively short period of time to ensure accurate and reliable separations.

Currently, a major limitation in the production and sale of pre-cast polyacrylamide electrophoresis gels is the relatively short shelf-life, usually up to about three months. This is thought to be due to the hydrolysis of the amide groups in polyacrylamide to the carboxylic acid derivative in alkaline conditions [Geisthardt & Kruppa, Polyacrylamide Gel Electrophoresis: Reaction of Acrylamide at Alkaline pH with Buffer Components and Proteins *Anal. Biochem.* 160, 184–191 (1987)]. This hydrolysis is manifested in the gels as a loss of resolution of separated molecules, change in the migration distances of the separated molecules and reduced intensity of protein staining.

Typically, gels are prepared using alkaline buffers and run under alkaline conditions, usually around pH 8.9. A buffer system using Tris(hydroxymethyl)aminomethane and hydrochloric acid (Tris-HCl) developed by Laemmli [Cleavage of Structural Proteins During the Assembly of the Head of Bacteriophage T4 *Nature* 227, 680–686 (1970)], is a typical choice for "standard' polyacrylamide gels in denaturing conditions. Although loss of stability in polyacrylamide gels occurs faster in alkaline conditions, this was thought to be unavoidable in standard gels. In principle, if the pH of the buffer in which the polymer network is formed could be lowered to around neutral, then the hydrolysis of the gel should be greatly reduced and so the gels should remain stable and useful for a longer period of time. Unfortunately, it has been difficult to find inexpensive chemical systems with an effective buffering capacity around neutral pH that are compatible with a polyacrylamide medium and suitable for gel electrophoresis and which do not have any effects that would cause a loss of stability through other interactions.

The most common buffer system used for sodium dodecyl sulfate polyacrylamide gel electrophoresis (SDS-PAGE) is that published by Ormstein [Disc Electrophoresis, 1, Background and Theory *Ann. New York Acad. Sci.* 121, 321–349 (1964)] and modified by Laemmli. This system uses a discontinuous electrophoresis system composed of a 'stacking' gel with a Tris concentration of 0.125 M at pH 6.8 and a 'resolving' gel with a Tris concentration of 0.375 M at pH 8.8. The change in pH causes the proteins in the gel to 'stack' or concentrate into a fine line in the lower pH gel and then 'resolve' or spread out in the higher pH gel. The stacking gel is a short zone and the resolving gel is a longer zone in the gel. The other common Tris-HCl system is that of Schagger and von Jagow [Tricine-Sodium Dodecyl Sulfate-Polyacrylamide Gel Electrophoresis for the Separation of Proteins in the Range from 1 to 100 kDa *Anal. Biochem* 166, 368–379 (1987)] who used a stacking gel of 0.75 M Tris at pH 8.45 and a resolving gel of 0.9 M at pH 8.45. Some reports have been made of the use of the Tris-HCl system below these pH values. Reisfield and Williams [Disc Electrophoresis in Polyacrylamide Gels: Extension to New Conditions of pH and Buffer *Ann. N.Y. Acad. Sci.* 121, 373–381 (1964)] have used Tris-HCl at a pH of 7.5, but their Tris concentration was very low (around 0.08 M) and their electrode buffer was Tris-diethylbarbituric acid. The present inventors have found that using Tris at these very low concentrations and at low pHs in more common electrophoresis of buffers leads to a distortion of bands and lack of resolution. King et al [Electrophoretic Conditions for High Resolution Citrus Isozymes in Polyacrylamide Gel Electrophoresis *Electrophoresis* 16, 32–38 (1995)] have used traditional concentrations of Tris (0.375 M) at pH 7.5. To reach the lower pH levels at this high concentration of Tris involves the addition of a large amount of hydrochloric acid leading to high conductivity in the gel. When the conductivity of the gel is high, the gels run very slowly in traditional electrode buffers.

A number of different gel buffer systems have been proposed for use at or around neutral pH that do not involve the use of Tris-HCl. The most common buffer system at neutral pH is the phosphate system of Shapiro [*Biochem. Biophys. Res. Commun.* 28, 815 (1967)] modified by Weber and Osborn [The Reliability of Molecular Weight Determinations by Dodecyl Sulfate-Polyacrylamide Gel Electrophoresis *J. Biol. Chem.* 244(16), 4406–4412 (1969)]. Other buffer systems include Bis-Tris-HCl [Moos et al Reproducible High Yield Sequencing of Proteins Electrophoretically Separated and Transferred to an Inert Support *J. Biol. Chem.* 263(13), 6005–6008 (1988)], Tris-Acetate [Patton et al Tris-Tricine and Tris-Borate Buffer Systems Provide Better Estimates of Human Mesothelial Cell Intermediate Filament Protein Molecular Weights than the Standard Tris-Glycine System *Anal. Biochem.* 197, 25–33 (1991)], glycylglycine-NaOH [Hoffmann & Chalkley A Neutral pH Acrylamide Gel Electrophoretic System for Histones and Other Basic Proteins *Anal. Biochem.* 76, 539–546 (1976)], 1,4 piperazine-bis-(ethane sulfonic acid) (PIPES) —$Na_3PO_4$ [Davis &

Gregerman Separation of Thyroxin (T$_4$)-Binding Proteins of Human Serum in Polyacrylamide Gel at pH 7.4. I. Effect of pH on Distribution of Tracer Quantities of T$_4$ *J. Endocr.* 30, 237–245 (1970)], 4-(2-hydroxyethyl)piperazine-1-ethanesulphonic acid (HEPES)/2-(N-morpholino) ethanesulphonic acid (MES)/3-(N-morpholino)propane sulphonic acid (MOPS)/Bicine-NaOH [12], MOPS-KOH [Thomas & Hodes A New Discontinuous Buffer System for the Electrophoresis of Cationic Proteins at Near-Neutral pH *Anal. Biochem.* 118, 194–196 (1981)] and Histidine-HCl/ Tris-Citrate [King et al Electrophoretic Conditions for High Resolution Citrus Isozymes in Polyacrylamide Gel Electrophoresis *Electrophoresis* 16, 32–38 (1995)].

The buffering capacity of Tris-HCl is reduced at neutral pH and so commercially available pre-cast gels with longer shelf lives employ different buffer systems. U.S. Pat. No. 3,948,743 (Bio-Rad Laboratories, 1976) discloses the use of a strongly ionisable neutral salt in a concentration of 0.0005 N to 1.0 N at a pH of between 6 and 8. The neutral salt is preferably ammonium sulfate. The gels are then 'pre-run' in the buffer that is desired for separation to remove the salt before application of the sample. It would appear, however, that this method has not been commercialised due to the inconvenience of having to pre-run the gels before they are useful for electrophoresis.

U.S. Pat. No. 4,415,655 and U.S. Pat. No. 4,481,094 (TechAmerica Group Inc., 1983 and 1984) disclose the use of a salt of 2-amino-2-methyl-1,3-propanediol at a pH of 6.4 to 7.3 in combination with 2-amino-2-methyl-1,3-propanediol turine as an electrolyte buffer at a pH of 8.0 to 10.0.

U.S. Pat. No. 5,578,180 and U.S. Pat. No. 5,922,185 (Novel Experimental Technology, 1996 and 1999) disclose gels containing a buffer comprised of a primary organic amine or substituted amine with a pK$_a$ near neutrality, titrated with hydrochloric acid or acetic acid to a pH between 5.5 and 7.5. The amine is preferably Bis-(2-hydroxyethyl)iminotris(hydroxymethyl)methane (Bis-Tris). The system runs with the gel and buffer at a pH around neutral. U.S. Pat. No. 6,059,948 is a continuation-in-part of these patents and discloses the use of a similar gel buffer consisting of an amine with pK$_a$ near neutrality and a zwitterionic base with a pK$_b$ between 6 and 9 with the buffer having a pH between pH 5.5 and 7.5.

U.S. Pat. No. 5,464,516 (Hymo Corporation, Atto Corporation, 1995) discloses gels which contain a buffer comprised of an acid, amine and an ampholyte that has the same number of anionic and cationic groups in each single molecule. The pH of these gels is between 4 and 7.5 and have been designed to give a wide separation range and stability. This patent mentions that lowering the pH and Tris concentration in conventional gel systems does not allow sufficient movement of proteins so is not suitable for use in electrophoretic separation of compounds.

The present inventors have now surprisingly found that by manipulating the conventional Tris-HCl buffer system, stable gels can be prepared that have comparable separation characteristics as standard gels but having the advantage of long shelf-life.

DISCLOSURE OF INVENTION

The present invention relates a gel system with a substantially neutral gel buffer system which assists in limiting the hydrolysis of the polymer network of the gel. Modification of conventional Tris-HCl buffer systems resulted in increased stability of the gel during storage. Importantly, in use the gels have minimal variation in migration distances of the proteins and increased retention of band sharpness over time.

In a first aspect, the present invention provides a polyacrylamide gel utilising a buffer system comprising Tris (hydroxymethyl)aminomethane at a concentration range of about 0.15 to 0.25 M titrated with hydrochloric acid to a pH between about 6.5 and 7.5.

Preferably, the gel comprises Tris(hydroxymethyl) aminomethane at about 0.18 to 0.22 M and having a pH of about 6.8 to 7.2. More preferably, the gel comprises Tris (hydroxymethyl)aminomethane at about 0.20 M and having a pH of about 7.0.

The gels produced according to the present invention are substantially relatively stable to polyacrylamide hydrolysis during storage for at extended periods. The gels have an acceptable shelf-life of at least about six months, preferably at least about nine months and even more preferably at least about 12 months after storage at about or around 4° C. An acceptable shelf-life can be determined by the gel producing a resolving protein separation migration pattern under electrophoresis conditions which is similar to or better than the degree of resolution of the same or similar sample using standard Tris/HCl gels. Typically, there is little or no significant deterioration in the degree of separation or sharpness of protein bands in the gels after prolonged storage times prior to use.

The polyacrylamide gels according to the present invention are cross-linked acrylamide formed by treating acrylamide with a cross-linking agent, usually N,N'-methylene-bis-acrylamide (Bis)under suitable initiating conditions. Although Bis is the cross-linker of choice for most standard gel-forming processes, a number of other cross-linking agents have been developed or are being developed. Examples include Piperazine diacrylamide (PDA) and N,N'diallyl-tartardiamide (DATD). The present invention is therefore applicable to all forms of polyacrylamide, irrespective of the cross-linking agent.

In a second aspect, the present invention provides a method of preparing a polyacrylamide gel, the method comprising polymerising acrylamide in the presence of a cross-linking agent, water, a buffer system for the polyacrylamide gel and a polymerisation means;

wherein the buffer system comprises Tris(hydroxymethyl) aminomethane at the concentration range of about 0.15 to 0.25 M titrated with hydrochloric acid to a pH between about 6.5 and 7.5.

Preferably, the gel comprises Tris(hydroxymethyl) aminomethane at about 0.18 to 0.22 M and having a pH of about 6.8 to 7.2. More preferably, the gel comprises Tris (hydroxymethyl)aminomethane at about 0.20 M and having a pH of about 7.0.

The gels produced according to the present invention are substantially relatively stable to polyacrylamide hydrolysis during storage for at extended periods. The gels have an acceptable shelf-life of at least about six months, preferably at least about nine months and even more preferably at least about 12 months after storage at about or around 4° C. An acceptable shelf-life can be determined by the gel producing a resolving protein separation migration pattern under electrophoresis conditions which is similar to or better than the degree of resolution of the same or similar sample using standard Tris/HCl gels. Typically, there is little or no significant deterioration in the degree of separation or sharpness of protein bands in the gels after prolonged storage times prior to use.

The polyacrylamide gels according to the present invention are cross-linked acrylamide formed by treating acrylamide with a cross-linking agent, usually N,N'-methylene-bis-acrylamide (Bis)under suitable initiating conditions. Although Bis is the cross-linker of choice for most standard gel-forming processes, a number of other cross-linking agents have been developed or are being developed. Examples include Piperazine diacrylamide (PDA) and N,N'diallyl-tartardiamide (DATD). The present invention is therefore applicable to all forms of polyacrylamide, irrespective of the cross-linking agent.

Preferably, the polymerisation means is by redox type initiator using ammonium persulphate (APS) and N,N,N', N'-tetramethylethelenediamine (TEMED). Other free-radical initiator systems suitable for polymerising acrylamide gels including redox, thermal, photoactivation systems would also be suitable for the present invention.

In a third aspect, the present invention provides an apparatus for use in gel electrophoresis, the apparatus comprising a gel according to the first aspect of the present invention adapted to be inserted in an electrophoresis apparatus.

The apparatus can be any standard electrophoresis apparatus housing a gel according to the present invention. The apparatus typically comprises one or more receptacles for electrophoresis buffer electrodes positioned in contact with the electrode buffer, and a housing to accept an arrangement for the electrophoresis gel, typically a cassette arrangement.

In a fourth aspect, the present invention provides a method of performing electrophoresis, the method comprising:

(a) applying a sample containing one or more compounds to be separated to the gel of an electrophoresis apparatus according to the third aspect of the present invention;

(b) providing an electrode buffer; and (b) subjecting the gel to an electric field for sufficient time such that at least one compound in the sample is caused to move into the gel.

In one preferred form, the electrode buffer comprises Tris(hydroxymethyl) aminomethane and 4-(2-hydroxyethyl)piperazine-1-ethanesulphonic acid (HEPES). Preferably, the electrode buffer has a concentration of about 0.05 to 0.125 M and has a pH of about 7.5 to 8.5.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

In order that the present invention may be more clearly understood preferred forms will be described with reference to the following examples and drawings.

MODE(S) FOR CARRYING OUT THE INVENTION

Figure 1:
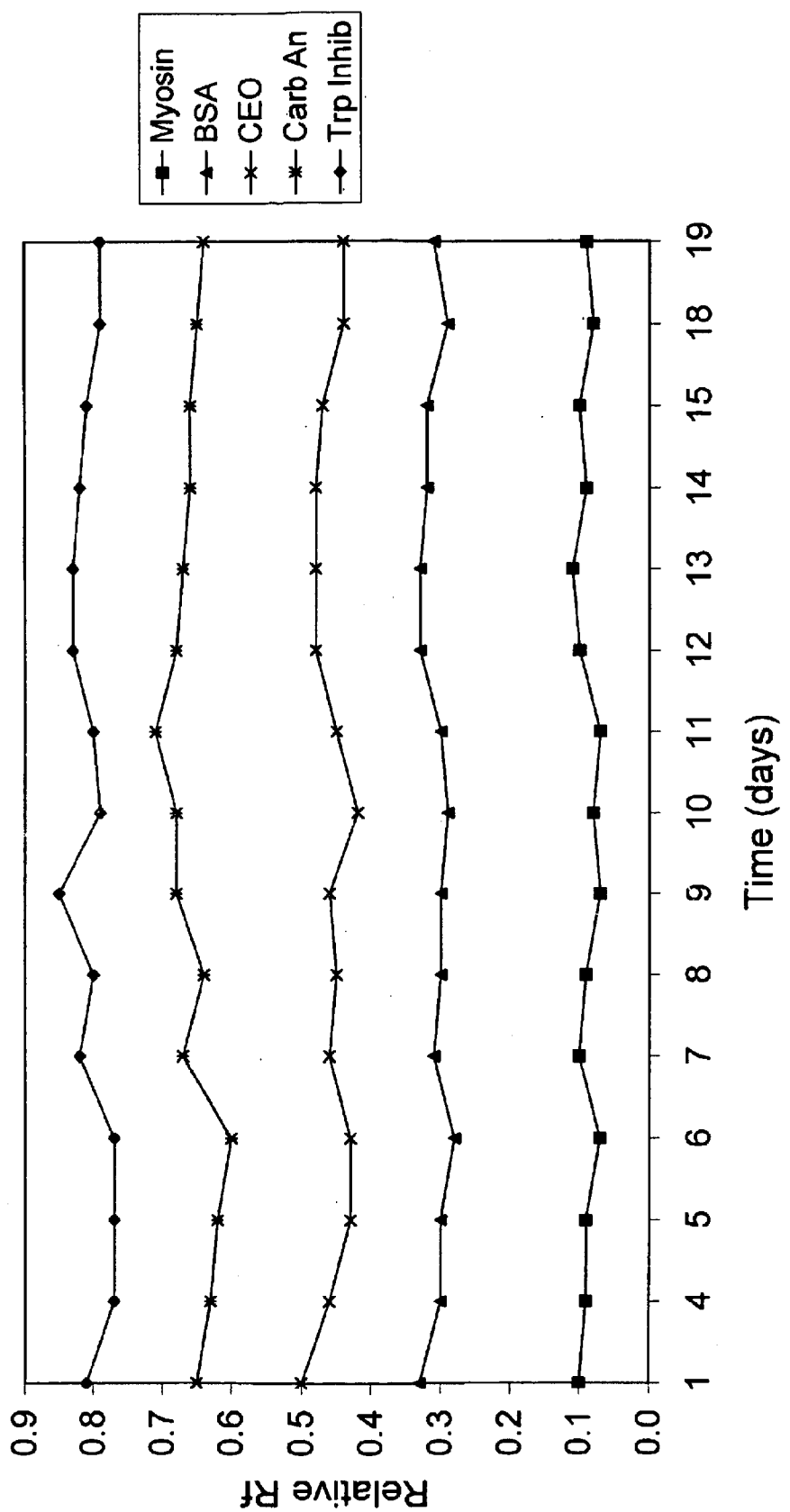
FIG. 1 shows separation of standard proteins in gels produced according to the present invention stored under accelerated storage conditions over various periods.

The present invention involves the use of a Tris-HCl buffer system at a pH in the range of about 6.5 to 7.5. Under this pH range, the polymer network of the gel is no longer subject to alkaline conditions where hydrolysis can occur. One result is the gels have a longer storage potential or 'shelf-life'.

Methods

Gel Recipe

For the preparation of a 12% homogeneous gel, the following recipe was used. A stacking gel solution (5%T/4%C) was prepared by mixing 4.8 g of acrylamide, 0.2 g of Bis and 2.42 g of Tris with 5 mL of glycerol in 60 mL of distilled water. The pH of this solution was adjusted to 7 by adding approximately 12 mL of 6 M hydrochloric acid. The final solution was made up to 100 mL with distilled water.

A resolving gel solution (12%T/4%C) was prepared by mixing 10.22 g of acrylamide, 0.43 g of Bis and 2.42 g of Tris with 10 mL of glycerol in 60 mL of distilled water. The pH of this solution was adjusted to 7.00 by adding approximately 12 mL of 6 M hydrochloric acid. The final solution was made up to 100 mL with distilled water.

Results

To determine the combinations of Tris-HCl concentration and pH that provide acceptable results, a series of experiments were performed where the Tris concentration was varied in the range 0.100–0.375 M and the pH in the range 6.5–8.5. An initial experiment was performed where gels were made with an acrylamide concentration of 4–20% and a Tris concentration of 0.375 M at pH values of 8.5, 8.0 and 7.5. The stability of these gels was examined in the Tris-Glycine the electrophoresis of buffer system of Laemmli. It was found that the stability did improve with lower pH. The conductivity of the lower pH gels, however, was higher and this led to a lengthening of the time for electrophoresis in the Tris-Glycine system to unacceptable periods. Furthermore, a distortion of the normal relative migration distances for standard proteins was observed. When a similar experiment was performed where the concentration of Tris was reduced to 0.2 M at pH 8.0, it was found that the relative migration of the proteins was similar to that in the Laemmli system using the same time for electrophoresis. The stability of the gels was also extended from 4 months to 6 months. The conductivity of these gels was comparable to that of the standard Laemmli gels with Tris concentration 0.375 M at pH 8.5.

To try and 'match' the Laemmli solution conductivities at pH 6.5, 7.0 and 7.5, low concentrations of Tris were required. When 0.1 and 0.15 M solutions were tried, the buffering effect of Tris was greatly reduced and distorted protein patterns were observed. This can be explained as the buffering capacity of Tris is weak at these pH values. Surprisingly, the present inventors found that if the concentration of Tris is slightly higher (in the range 0.15 to 0.25 M) a balance can be found where Tris is still acting as a buffer so that the protein migration pattern is satisfactory but the conductivity of the gel is low enough to allow a faster electrophoresis time. This finding is quite different from what would be expected in these buffer systems. Furthermore, the prior art teaches that buffer systems other than Tris-HCl must be used to obtain similar results. As a result, others were forced to carry out a lot of work to change the chemical components of the gel buffer system to obtain gels at neutral pH which function acceptably in electrophoresis separations.

The experiments outlined above were all carried out using the standard Laemmli Tris-Glycine as the electrophoresis of buffer formulation. Gels can be made and run in Tris-Glycine as the electrophoresis of buffer to give similar migration distances for standard proteins. These patterns can be manipulated by varying the %T and %C in the gels to give the desired pattern. In Tris-Glycine buffer, the voltage for electrophoresis usually needs to be slightly higher than for 'standard' gels to give the same electrophoresis time.

Gels according to the present invention can also be used with a wide variety of electrode buffers. Gels were compatible with the 'traditional' SDS electrode buffers such as that of Laemmli (Tris-Glycine) and Schagger and von Jagow (Tris-Tricine). A range of other systems have also been tested including the combinations Tris-HEPES, Tris-Bicine, Tris-(N-[2-Hydroxyethyl]piperazine-N'-[3-propanesulfonic acid] (EPPS), Imidazole-HEPES, Tris-MES, Tris-MOPS and MES-Imidazole. In use, the gels behave differently in these various electrode buffer systems to produce differing but quite acceptable separation migration patterns can be achieved. Accordingly, there is a distinct flexibility for the use of the gels according to the present invention. The resolution of proteins in all of the electrode buffer systems tested was found to be excellent. It will be appreciated that the electrode buffer systems that can be used are not limited to the examples that have been mentioned. From the favorable results with many quite different electrode buffer systems, other buffer systems are likely to be compatible with the gels according to the present invention.

The gel buffer system according to the present invention performs particularly well in a 100 mM Tris-HEPES electrode buffer system. All acrylamide concentrations tested gave electrophoresis times of around 30 minutes under standard conditions of electrophoresis voltage of 200 V at room temperature. The resolution was comparable or superior to that found in other commercially available pre-cast gels. If a gradient of 4–20% acrylamide was used in the gel, then proteins can be separated between the molecular masses of 200 to 6.5 kDa.

By way of comparison, gels were made with Tris-Acetate buffer at a concentration of 0.2 M and a pH of 7.0. These gels were tested both in the Tris-Glycine and in the Tris-HEPES systems and were found to have a longer electrophoresis of time to the gels of the present invention. Furthermore, there was no improvement in resolution patterns or separation qualities compared with the gels according to the present invention.

The present invention provides a remarkable improvement in the stability of Tris-HCl gels. Gels run in Tris-Glycine exhibited excellent stability when used after more than 12 months of storage at 4° C. The gels of the present invention remained stable in both the relative migration distance of the proteins and in the sharpness of the protein bands over storage time. The relative migration of standard proteins in a wide range molecular weight markers in 4–20% acrylamide gels did not change significantly after 12 months storage. In standard gels, there was significant unacceptable change in the migration value and resolution with length of storage time. A small amount of change can be acceptable to the end user but there is a distinct advantage in having substantially no change in gels stored over long periods.

The reproducibility of the migration pattern in gels according to the present invention was excellent with storage time as well as within and between different batches of gels. There was no significant change in migration with time over 12 months for a gel made with 4–20%T acrylamide with 0.2 M Tris at pH 7.0 according to the present invention. In contrast, there was significant and unacceptable migration change with time in a control gel with 4–20%T acrylamide with 0.375 M Tris at pH 8.5. The acceptable shelf-life of the control gel was limited to only 4 months.

The sharpness of the bands also varied very little with storage time of the gels according to the present invention. There was some slow loss of sharpness when the gels were electrophoresed in Tris-Glycine buffer after 12 months of storage. This loss of sharpness, however, was slow and did not become as significant as the loss of bands that was seen in prior art gels that were used past their recommended shelf life under the same electrophoresis conditions. Gels according to the present invention that were 12 months old when run in Tris-HEPES buffer still produced very sharp bands.

The present inventors have found that when the gels were run in Tris-HEPES buffer and then stained with any conventional stain, the staining time and quality was comparable to other commercially available gels stored within the manufacturer's recommended time. The gels according to the present invention were compatible with the commonly used colloidal and non colloidal forms of Coomassie Brilliant Blue staining. When the highly sensitive silver diamine staining technique was used, the gels according to the present invention had a clear, glassy background. The lack of background staining is very desirable in electrophoresis gels. Other buffer systems that replace Tris to provide gels at neutral pH use chemicals that react during silver staining to give a yellow background that reduces the sensitivity of the stain. As the gels of the present invention do not suffer from unacceptable backgrounds during staining, this is another benefit of the present invention over the prior art.

Any suitable initiation system can be used to induce polymerisation of the gels according to the present invention. These systems include, but are not limited to, redox systems such as ammonium persulfate (APS) and N,N,N', N'-tetramethylethylenediamine (TEMED), photoinitiation systems such as riboflavin, thermal initiation using (APS) as well as other less commonly used systems.

In one embodiment of the invention, the gels were made of polyacrylamide using standard techniques. Acrylamide was mixed with a cross-linker (N,N'-methylene bisacrylamide) and a solution of Tris such that the concentration of Tris in the final solution was 0.2 M. The solution was adjusted with HCl such that the pH of the solution was 7.0. Initiation of the polymerisation was achieved by redox initiation with APS and TEMED. A typical example of the acrylamide concentrations in these gels was a stacking gel comprised of 5%T/4%C and resolving gel of 10%T/3%C. Any suitable acrylamide concentrations can, however, be used in the present invention.

Stability Results

Accelerated stability trials showed that gels produced by the present invention were more stable than conventional gels. The test gels were stored at 37° C. and sampled each day. The migration values of specific proteins were determined and changes assessed over time.

Figure 2:
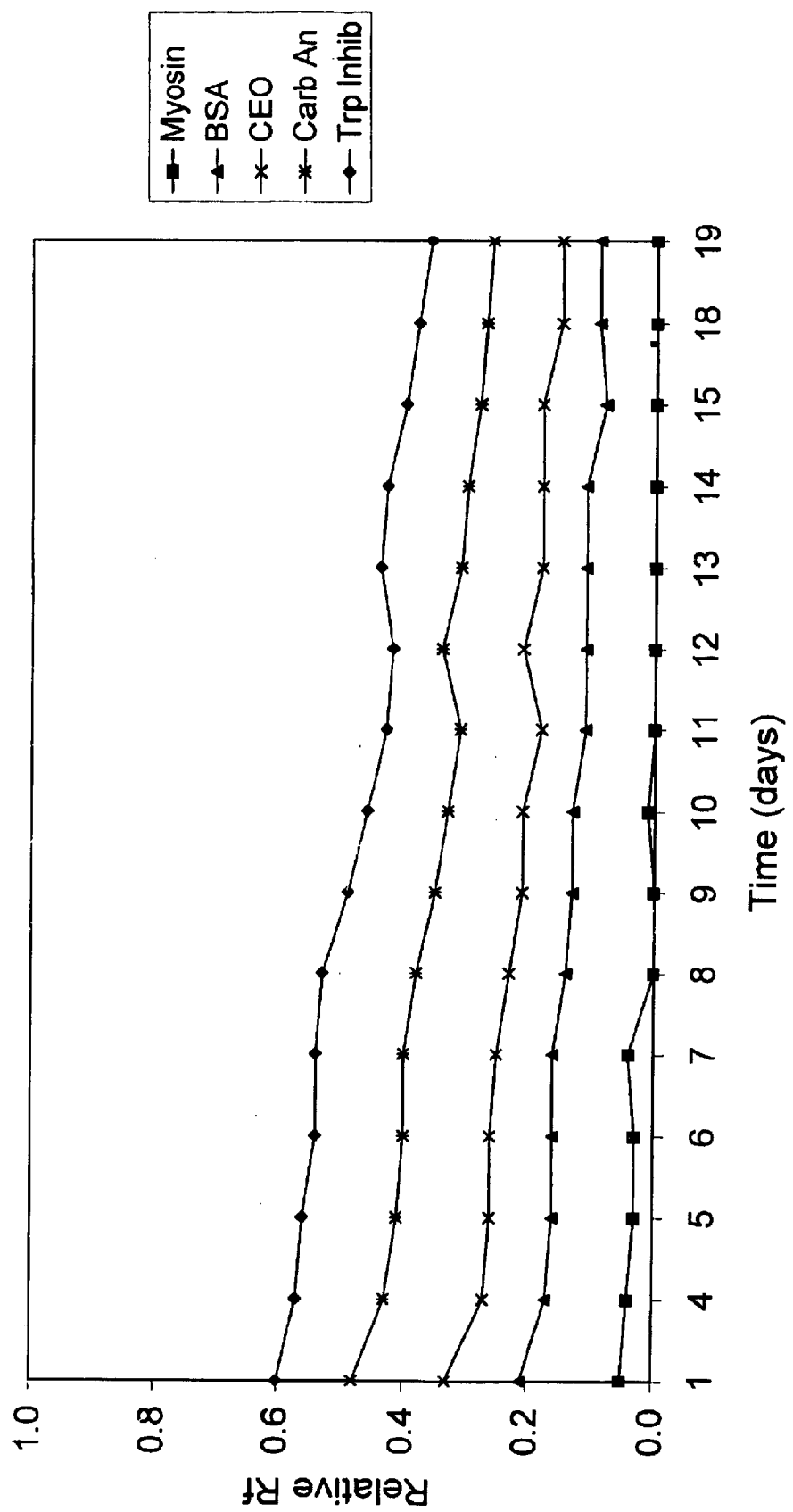
FIG. 2 shows separation of standard proteins in gels produced by standard methods stored under accelerated storage conditions over various periods.

The gels produced according to the present invention tested were outstanding in the stability of the migration values of the proteins in the gel. FIGS. 1 and 2 show a neutral pH gel with a Tris concentration of 0.2 M (FIG. 1) compared to a conventional gel (FIG. 2) in an accelerated stability trial (37° C. storage). The results in FIG. 1 show that the protein migration values do not substantially change with time in gels made according to the present invention. The gels also did not suffer from loss of bands or loss of resolution/band sharpness. The accelerated stability trials showed that the new gels lasted longer than the control gels which were also stored at the elevated temperature. The distinctive results found in accelerated studies indicate that gel stability will be sustained during storage at conventional storage temperatures (around 4° C.).

Figure 3:
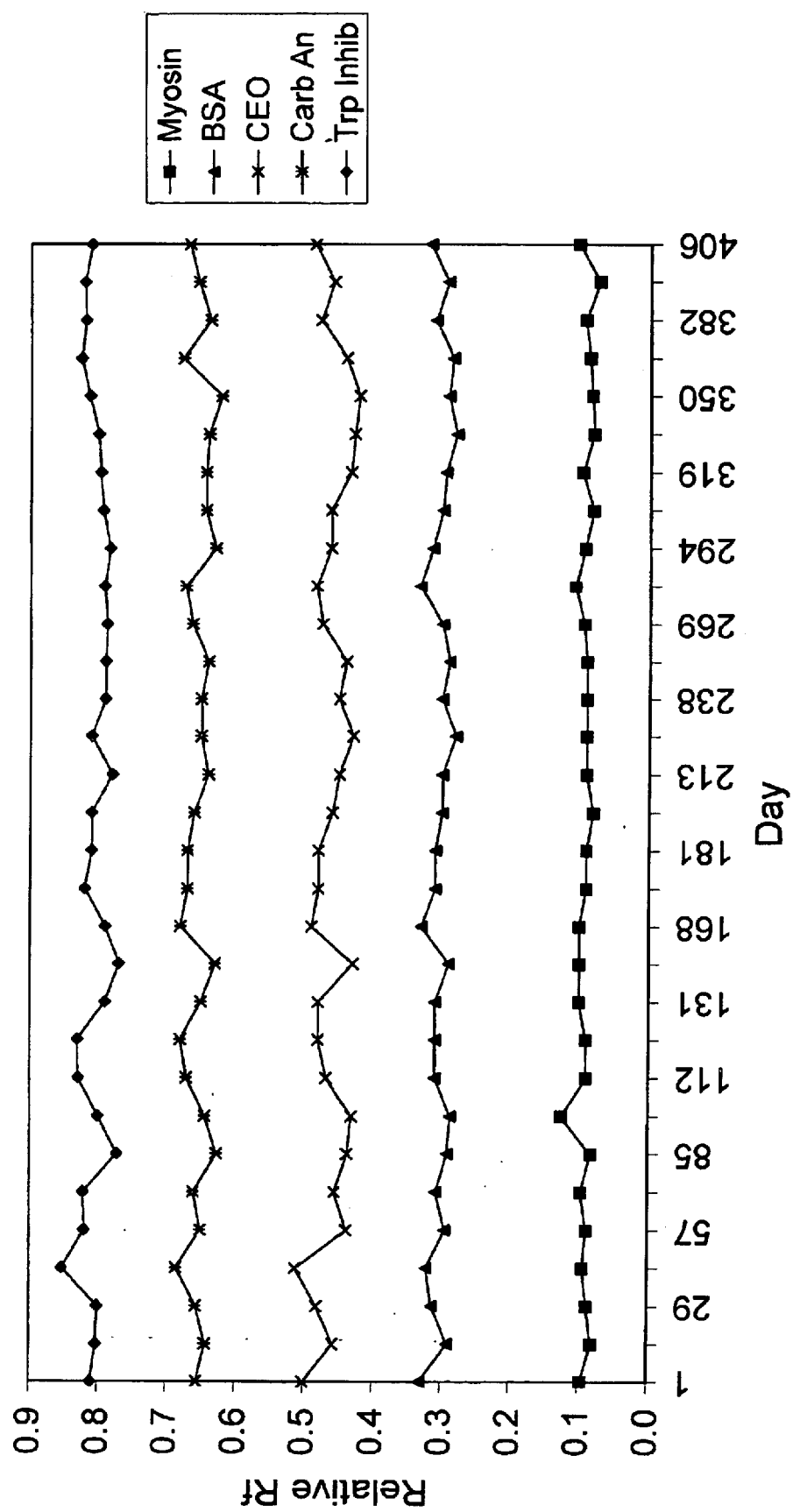
FIG. 3 shows separation of standard proteins in gels produced according to the present invention stored over various periods.
Figure 4:
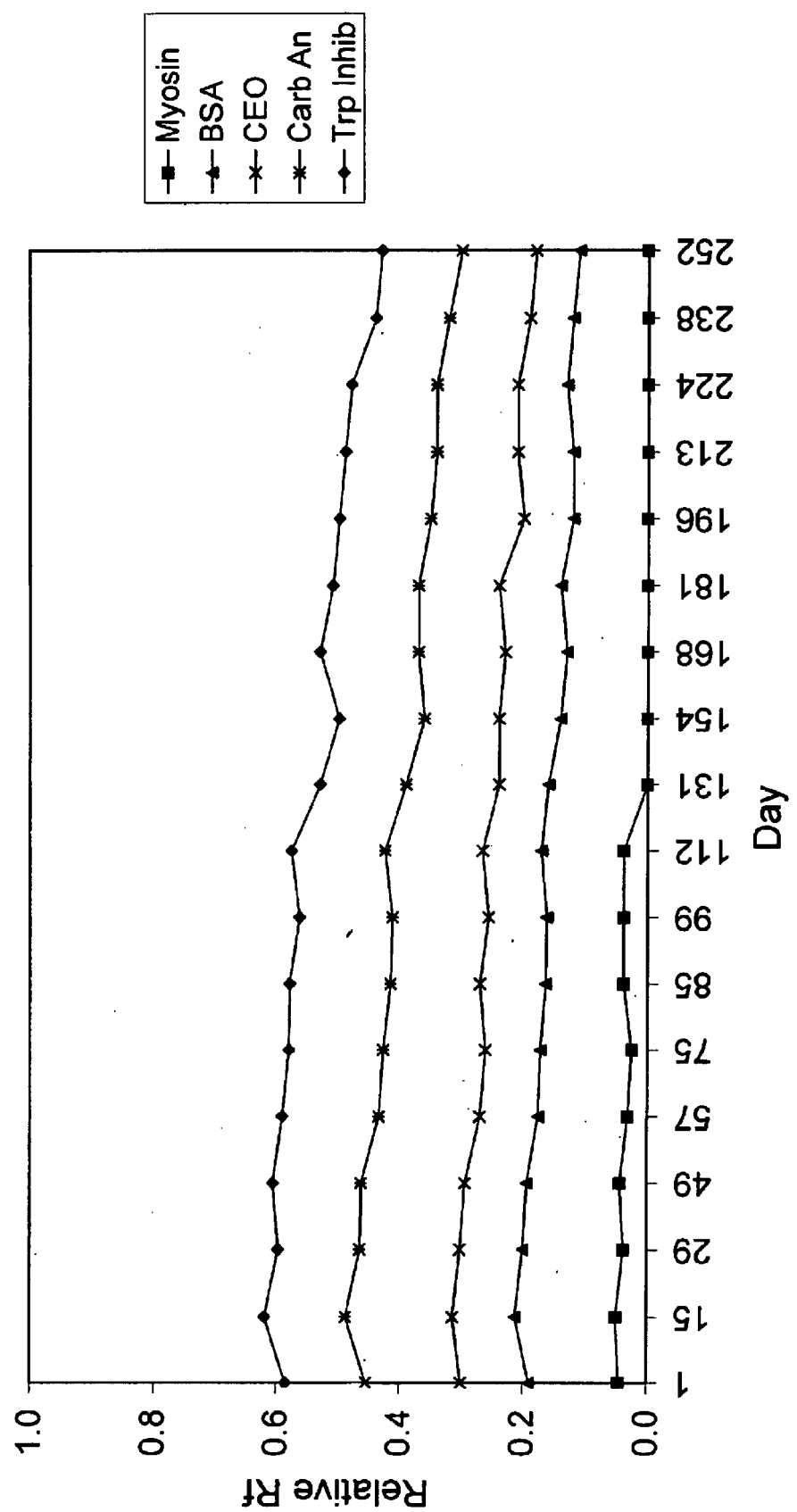
FIG. 4 shows separation of standard proteins in gels produced by standard methods stored over various periods.

Further stability experiments using real time (4° C. storage) of gels produced according to the present invention confirmed the findings of the accelerated studies. Gels having a pH of about 7.5 and lower Tris concentration showed that the stability was in fact lengthened by approximately 50% when stored at 4° C. for extended periods. FIG. 3 shows the change in protein migration in gels produced according to the present invention for various times more than 12 months storage. FIG. 4 shows the change in protein migration in conventional gels stored at various times over six months. As can be clearly seen from the Figures, the migration patterns of a number of proteins did not substantially change in the gels produced according to the present invention over the storage time tested. In contrast, gels produced having higher alkaline pH showed a decrease in performance over the six month test period. It can be seen from these results that a longer shelf-life was achieved in gels with a lower pH and a reduced Tris concentration produced according to the present invention.

EXAMPLES

In the following examples, gels were cast in mini gel cassettes (gel size 8 cm×6 cm×1 mm). The solutions used in polymerisation were prepared by mixing stock solutions of acrylamide/Bis and Tris-HCl and adding water to dilute to the appropriate concentration.

Example 1

A polyacrylamide gel was cast with an acrylamide concentration of 5%T/4%C in the stacking region and 10%T/3%C in the resolving region of the gel. The concentration of Tris in the gel was 0.2M and the pH of the gel was adjusted to 7.0 using HCl. Two different samples were separated on this gel using an electrode buffer of Tris (25 mM), Glycine (191 mM) and SDS (0.1%). The protein samples were snow pea protein and wide range molecular weight marker which was a commercially available marker containing samples denatured by the addition of DTT. The marker was reconstituted in water as per the manufacturer's instructions. The gel was electrophoresed for 90 minutes at a voltage of 200V. Trypsinogen, trypsin inhibitor and aprotinin in the wide range marker stayed with the tracking dye and moved off the end of the gel.

The proteins in the standard that remained on the gel were Myosin (Rabbit Muscle, 205 kDa), β-Galactosidase (E. coli, 116 kDa), Phosphorylase b (Rabbit Muscle, 97 kDa), Fructose-6-phosphate Kinase (Rabbit muscle, 84 kDa), Albumin (Bovine Serum, 66 kDa), Glutamic Dehydrogenase (Bovine Liver, 55 kDa), Ovalbumin (Chicken Egg, 45 kDa), Glyceraldehyde-3-phosphate Dehydrogenase (Rabbit muscle, 36 kDa), Carbonic Anhydrase (Bovine Erythrocytes, 29 kDa), Trypsinogen (Bovine Pancreas, 24 kDa), Trypsin Inhibitor (Soybean, 20 kDa) and α-lactalbumin (Bovine Milk, 14.2 kDa). The markers were distributed along the gel such that the myosin was about 10% of the way down the gel and the lactalbumin was about 80% of the way down the gel.

The current generated in the electrophoresis of the gel varied from 100 to 25 mA over the period of the run.

Example 2

A polyacrylamide gel was cast with an acrylamide concentration of 5%T/4%C in the stacking region and 10%T/3%C in the resolving region of the gel. The concentration of Tris in the gel was 0.2 M and the pH of the gel was adjusted to 7.0 using HCl. A sample of snow pea protein and wide range molecular weight marker were separated on this gel using an electrode buffer of Tris (100 mM) and HEPES (100 mM) and electrophoresed for 30 minutes at a voltage of 200V. Trypsin inhibitor, lactalbumin and aprotinin stayed with the tracking dye and moved off the end of the gel.

The proteins in the standard that remained on the gel were Myosin (Rabbit Muscle, 205 kDa), β-Galactosidase (E. coli, 116 kDa), Phosphorylase b (Rabbit Muscle, 97 kDa), Fructose-6-phosphate Kinase (Rabbit muscle, 84 kDa), Albumin (Bovine Serum, 66 kDa), Glutamic Dehydrogenase (Bovine Liver, 55 kDa), Ovalbumin (Chicken Egg, 45 kDa), Glyceraldehyde-3-phosphate Dehydrogenase (Rabbit muscle, 36 kDa), Carbonic Anhydrase (Bovine Erythrocytes, 29 kDa), Trypsinogen (Bovine Pancreas, 24 kDa) and Trypsin Inhibitor (Soybean, 20 kDa). The standards were distributed along the gel such that the myosin was about 10% of the way down the gel and the lactalbumin was about 80% of the way down the gel.

The current generated in the electrophoresis of the gel varied from 170 mA per gel to 70 mA per gel over the period of the run.

Example 3

A polyacrylamide gel was cast with an acrylamide concentration of 5%T/4%C in the stacking region and a gradient from 5%T/2.5%C to 20%T/5%C in the resolving region of the gel. The gel was at pH 7.0 with a Tris concentration of 0.2 M where the pH was adjusted using HCl. Samples of snow pea protein and commercially available wide range molecular weight marker were separated on the gel. The gel was electrophoresed for 30 minutes at a voltage of 200V in an electrode buffer comprised of Tris (100 mM) and HEPES (100 mM). Protein bands from Myosin (205 kDa) to Aprotinin (6.5 kDa) were resolved on the gel.

The proteins in the standard that remained on the gel were Myosin (Rabbit Muscle, 205 kDa), β-Galactosidase (E. coli, 116 kDa), Phosphorylase b (Rabbit Muscle, 97 kDa), Fructose-6-phosphate Kinase (Rabbit muscle, 84 kDa), Albumin (Bovine Serum, 66 kDa), Glutamic Dehydrogenase (Bovine Liver, 55 kDa), Ovalbumin (Chicken Egg, 45 kDa), Glyceraldehyde-3-phosphate Dehydrogenase (Rabbit muscle, 36 kDa), Carbonic Anhydrase (Bovine Erythrocytes, 29 kDa), Trypsinogen (Bovine Pancreas, 24 kDa), Trypsin Inhibitor (Soybean, 20 kDa) α-Lactalbumin (Bovine Milk, 14.2 kDa) and Aprotinin (Bovine, 6.5 kDa). The standards were distributed along the gel such that the myosin was about 11% of the way down the gel and the lactalbumin was about 84% of the way down the gel.

The current generated in the electrophoresis of the gel varied from 170 mA per gel to 70 mA per gel over the period of the run.

Example 4

A polyacrylamide gel was cast with an acrylamide concentration of 5%T/4%C in the stacking region and a gradient from 8%T/2.5%C to 14%T/5%C in the resolving region of the gel. The gel was at pH 7.0 with a Tris concentration of 0.2 M where the pH was adjusted using HCl. Samples of snow pea protein and commercially available wide range molecular weight marker were separated on the gel. The gel was electrophoresed for 30 minutes at a voltage of 200V in an electrode buffer comprised of Tris (100 mM) and HEPES (100 mM). Protein bands from Myosin (205 kDa) to Lactalbumin (14 kDa) were resolved on the gel.

The proteins in the standard that remained on the gel were Myosin (Rabbit Muscle, 205 kDa), β-Galactosidase (*E. coli*, 116 kDa), Phosphorylase b (Rabbit Muscle, 97 kDa), Fructose-6-phosphate Kinase (Rabbit muscle, 84 kDa), Albumin (Bovine Serum, 66 kDa), Glutamic Dehydrogenase (Bovine Liver, 55 kDa), Ovalbumin (Chicken Egg, 45 kDa), Glyceraldehyde-3-phosphate Dehydrogenase (Rabbit muscle, 36 kDa), Carbonic Anhydrase (Bovine Erythrocytes, 29 kDa), Trypsinogen (Bovine Pancreas, 24 kDa), Trypsin Inhibitor (Soybean, 20 kDa) and α-Lactalbumin (Bovine Milk, 14.2 kDa). The standards were distributed along the gel such that the myosin was about 10% of the way down the gel and the lactalbumin was about 85% of the way down the gel.

The current generated in the electrophoresis of the gel varied from 170 mA per gel to 70 mA per gel over the period of the run.

Example 5

A polyacrylamide gel was cast with an acrylamide concentration of 5%T/4%C in the stacking region and a gradient from 5%T/2.5%C to 20%T/5%C in the resolving region of the gel. The gel was at pH 7.0 with a Tris concentration of 0.2 M where the pH was adjusted using HCl. Samples of snow pea protein and commercially available wide range molecular weight marker were separated on the gel. The gel was electrophoresed for 20 minutes at a voltage of 200V in an electrode buffer comprised of Imidazole (100 mM) and MES (100 mM). Protein bands from Myosin (205 kDa) to Aprotinin (6.5 kDa) were resolved on the gel.

The proteins in the standard that remained on the gel were Myosin (Rabbit Muscle, 205 kDa), β-Galactosidase (*E. coli*, 116 kDa), Phosphorylase b (Rabbit Muscle, 97 kDa), Fructose-6-phosphate Kinase (Rabbit muscle, 84 kDa), Albumin (Bovine Serum, 66 kDa), Glutamic Dehydrogenase (Bovine Liver, 55 kDa), Ovalbumin (Chicken Egg, 45 kDa), Glyceraldehyde-3-phosphate Dehydrogenase (Rabbit muscle, 36 kDa), Carbonic Anhydrase (Bovine Erythrocytes, 29 kDa), Trypsinogen (Bovine Pancreas, 24 kDa), Trypsin Inhibitor (Soybean, 20 kDa), α-Lactalbumin (Bovine Milk, 14.2 kDa) and Aprotinin (Bovine, 6.5 kDa). The standards were distributed along the gel such that the myosin was about 5% of the way down the gel and the lactalbumin was about 75% of the way down the gel.

The current generated in the electrophoresis of the gel varied from 248 mA per gel to 180 mA per gel over the period of the run. The resolution of the proteins was adequate. The bands were not as sharp as in other systems but were still acceptable.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method of preparing a polyacrylamide gel, the method comprising polymerizing acrylamide in the presence of a cross-linking agent, water, a buffer system for the polyacrylamide gel and a polymerisation means, wherein the buffer system comprises Tris(hydroxymethyl)aminomethane at the concentration range 0.15 to 0.25 M titrated with hydrochloric acid to a pH between 6.5 and 7.5.

2. The method according to claim 1 wherein the cross-linking agent is N,N'-methylene-bis-acrylamide, and the polymerisation means is selected from redox systems using ammonium persulfate and N,N,N',N'-tetramethylethylenediamine (TEMED), photoinitiation systems using riboflavin, and thermal initiation using; ammonium persulfate.

3. The method according to claim 2 wherein the buffer system comprises Tris(hydroxymethyl)aminomethane at 0.18 to 0.22 M and having a pH of 6.8 to 7.2.

4. The method according to claim 3 wherein the buffer system comprises Tris(hydroxymethyl)aminomethane at about 0.20 M and having a pH of about 7.0.

5. The method according to claim 1 wherein the gel has an acceptable shelf-life of at least 6 months after storage at about 4° C., wherein the acceptable shelf-life being determined by the gel producing a resolving protein separation migration pattern under electrophoresis conditions.

6. The method according to claim 5 wherein the gel has an acceptable shelf-life of at least 9 months.

7. The method according to claim 6 wherein the gel has an acceptable shelf-life of about 12 months.

8. A method of performing electrophoresis, comprising:

(a) applying a sample containing one or more compounds to be separated to a gel of an electrophoresis apparatus whereby the apparatus contains a separating polyacrylamide gel composed of a non-stacking polyacrylamide gel and a buffer system composed of Tris(hydroxymethyl)aminomethane at the concentration range 0.15 to 0.25 M titrated with hydrochloric acid to a pH between 6.5 and 7.5;

(b) providing an electrode buffer, whereby the electrode buffer is Tris(hydroxymethyl) aminomethane and 4-(2-hydroxyethyl)piperazine-lethanesulphonic acid (HEPES); and (c) subjecting the gel to an electric field for sufficient time such that at least one compound in the sample is caused to move into the gel.

9. The method according to claim 8 wherein the Tris (hydroxymethyl) aminomethane and 4-(2-hydroxyethyl) piperazine-lethanesulphonic acid (HEPES) each have a concentration of 0.05 to 0.125 M and have a pH of 7.5 to 8.5.

* * * * *